United States Patent [19]

Mueller

[11] 4,282,158
[45] Aug. 4, 1981

[54] PROCESS FOR PRODUCING α,β-UNSATURATED KETONES

[75] Inventor: Richard A. Mueller, Glencoe, Ill.

[73] Assignee: G. D. Searle & Co., Skokie, Ill.

[21] Appl. No.: 125,302

[22] Filed: Feb. 27, 1980

Related U.S. Application Data

[62] Division of Ser. No. 61,732, Jul. 30, 1979.

[51] Int. Cl.$^3$ .................. C07C 49/23; C07C 49/235; C07C 49/242; C07C 49/248
[52] U.S. Cl. ................................ 260/347.8; 568/315; 568/347
[58] Field of Search .................... 260/347.8; 568/315, 568/347

[56] References Cited

U.S. PATENT DOCUMENTS

| | | | |
|---|---|---|---|
| 3,682,970 | 8/1972 | Henrick et al. | 260/347.8 X |
| 4,075,407 | 2/1978 | Mueller | 260/347.8 X |

*Primary Examiner*—Richard Raymond
*Attorney, Agent, or Firm*—Albert Tockman; W. Dennis Drehkoff

[57] ABSTRACT

Derivatives of α,β-unsaturated ketones having anticonvulsant activity and methods of their preparation from heterocyclic phosphonium salts and acyclic phosphoranes are disclosed.

8 Claims, No Drawings

PROCESS FOR PRODUCING α,β-UNSATURATED KETONES

This is a division of application Ser. No. 061,732, filed July 30, 1979.

This invention relates generally to α,β-unsaturated-β,ω¹-substituted ketones and their preparation. More particularly, the present invention relates to ketones having a phenyl, furyl or cyclohexyl radical at the β position and a pharmacologically acceptable nucleophilic radical at the ω¹ position, and their preparation by directly condensing an aromatic aldehyde, furfural or cyclohexanecarbaldehyde with a heterocyclic phosphonium salt in a neutral aprotic medium or by reacting the aldehyde with a previously formed phosphorane.

This invention is a pharmacologically active α,β-unsaturated-β,ω¹-substituted ketone having the formula

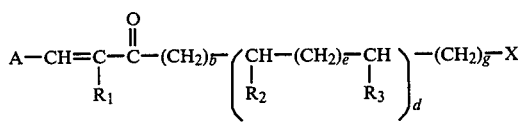

In formula I, A is a phenyl, furyl, furyl or cyclohexyl radical and may be unsubstituted or substituted with at least one nitro, halogen, hydroxyl, alkyl, alkoxy or trifluoromethyl radical, each alkyl radical containing from 1 to 6 carbon atoms and each alkoxy radical containing from 1 to 4 carbon atoms. $R_1$ is either hydrogen or a methyl radical. In addition b and g are each an integer from 0 to 5, d is 0 or 1, e is 0 or 1, and the sum of b, e, g and 2d is an integer from 3 to 5 such that cyclization is possible. $R_2$ and $R_3$ may be the same or different and can be a hydrogen, methyl, ethyl or phenyl radical, the phenyl radical being either unsubstituted or substituted with at least one halogen or alkyl radical containing from 1 to 3 carbon atoms. In the alternative, when e is 0, $R_2$ and $R_3$ may be interconnected to form, together with the intervening ethylene radical, a phenyl ring which is either unsubstituted or substituted with at least one halogen or alkyl radical containing from 1 to 3 carbon atoms. X is a fluoro, chloro, bromo, iodo or hydroxy radical.

The present invention is also a method for the preparation of these ketones when X is a halogen radical by the direct condensation of a heterocyclic phosphonium salt with an aromatic aldehyde, furfural or cyclohexanecarbaldehyde in an aprotic medium.

The ring in A may be unsubstituted or mono, di- or trisubstituted. Furthermore, the ring substituents in A can suitably be attached to carbon atoms in any ring positions therein. The alkyl radicals suitable for use as substituents in A are exemplified by methyl, ethyl, propyl, butyl, pentyl and hexyl, straight-chain and branched-chain radicals. Representatives of the alkoxy radicals useful as substituents in A are methoxy, ethoxy, propoxy and butoxy, straight-chain and branched-chain radicals. Preferably, A is a phenyl or furyl radical and more preferably is a nitro-or methoxy-substituted phenyl radical.

$R_1$ is preferably hydrogen. When $R_2$ or $R_3$ is, or together form, a phenyl ring, suitable substituents thereon include fluoro, chloro, bromo, iodo, methyl, ethyl, n-propyl and iso-propyl radicals. Preferably $R_2$ and $R_3$ are both hydrogen radicals, and b is an integer between 3 and 5; and d, e and g are 0.

Compounds to which this invention relates are useful by reason of their valuable pharmacological properties. Thus, for example, compounds of the present invention possess anticonvulsant activity as evident from the results of a standardized test of their capacity to prevent clonic convulsion induced in mice by pentyleneterazole. The procedure, a modification of one described by Chen et al., in Proc. Soc. Exp. Biol. and Med. 87, 337 (1954), is as follows: A selected dose (commonly but not invariably 100 mg/kg in the first instance) of the compound to be tested, suspended in 10 milliliters of a vehicle consisting of approximately 9.8 milliliters of physiological saline intimately mixed with 0.1 milliliter of propylene glycol and 0.1 milliliter of polysorbate 80, is administered intragastericaly (IG) or intraperitoneally (IP) to each of a group of 10 male Crl; COBS CD-1(ICR)BR mice, each weighing 18–28 grams.

After a selected interval of time (¼ ½, 1, 3, 6 or 24 hours), each mouse is challenged by intravenous infusion of 35 mg/kg of pentylenetetrazole (sufficient to induce clonic convulsions in control animals) administered as a 0.35 percent aqueous solution at a rate of approximately 0.1 milliliter per second. A compound is considered anticonvulsant at the selected dose if, after the selected time, clonic convulsions are prevented in at least 20 percent of the animals challenged.

1-(4-nitrophenyl)-7-chloro-1-hepten-3-one, 1-(3,5-dimethoxyphenyl)-8-bromo-1-octen-3-one, and 1-(3,5-dimethoxyphenyl)-7-chloro-1-hepten-3-one were anticonvulsant in this test ½ hour after IP administration of 64, 100 and 64 mg/kg, respectively.

The results are, of course, specified merely for the purposes of illustration and, accordingly, are not to be construed as either delimiting or exclusionary. Appropriate dosages in any given instance, of course, depend upon the nature and severity of the condition treated, the route of administration, and the species of mammal involved including its size and any individual idiosyncrasies which obtain.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinylalcohol, and thus tableted or encapsulated for convenient administration; alternatively, they may be dissolved or suspended in water or comparably in aqueous liquid. Parenteral administration may be effected via ster sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; See, for example, F. W. Martin et al., "Remington's Pharmaceutical Sciences", 14 Ed., Merck Publishing Co., Eaton, Pa. 1956.

The compounds of this invention, in which X in formula I is a halogen radical, can be prepared from a heterocyclic phosphonium salt of formula II.

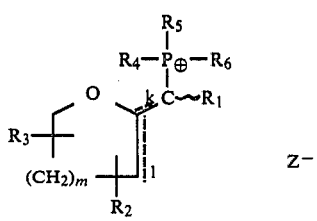

(II)

In formula II, $R_1$, $R_2$, and $R_3$ are defined hereinabove, and $R_2$ and $R_3$ are attached either to adjacent carbon atoms on the ring or to ring carbon atoms separated by only one carbon atom. Furthermore, m is an integer from 1 to 3, and one of k and l is a double bond and the other is a single bond. $R_4$, $R_5$ and $R_6$ may be the same or different and are each an alkyl radical containing 1 to 6 carbon atoms, a cycloalkyl radical containing 5 or 6 carbon atoms, or a radical having the formula

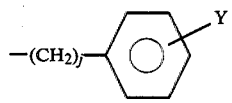

wherein j is an integer from 0 to 4 and Y is hydrogen, halogen, an alkyl radical containing 1 to 6 carbon atoms or an alkoxy radical containing 1 to 4 carbon atoms. $Z^-$ is a pharmacologically acceptable anion such as chloride, bromide, iodide, acetate, propionate, benzoate, tetrafluoroborate and trifluoromethylsulfonate.

The alkyl radicals suitable for use as $R_4$, $R_5$, $R_6$, and Y are exemplified by methyl, ethyl, propyl, butyl, pentyl and hexyl, straight-chain and branched-chain radicals. Representative alkoxy radicals suitable for use as Y are methoxy, ethoxy, propoxy, and butoxy, straight-chain and branched-chain radicals.

Thus the heterocyclic phosphonium salt starting material has formula III, IV or V depending upon whether m is 1, 2 or 3, respectively:

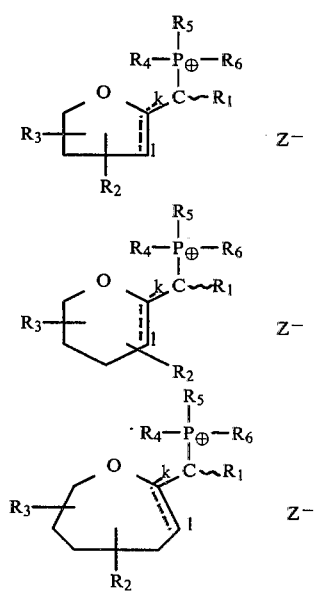

Suitable heterocyclic phosphonium salts with $R_2$ and $R_3$ being hydrogen and $z^-$ being a halogen anion and syntheses therefor, are disclosed in the applicant's U.S. Pat. No. 4,075,407, the entire disclosure of which is specifically incorporated herein by reference. When the syntheses of U.S. Pat. No. 4,075,407 are used, the products obtained can be a mixture of a pair of isomers of either formula III, IV or V depending on the starting material used. Thus, for example, when a product of formula IV is obtained, the products can be a mixture of [(5,6-dihydropyran-2-yl) methyl]-$R_4$,$R_5$,$R_6$-substituted phosphonium halide and [(tetrahydro-2H-pyran-2-ylidene)methyl]-$R_4$,$R_5$,$R_6$-substituted phosphonium halide which are shown by formulas VI and VII, respectively.

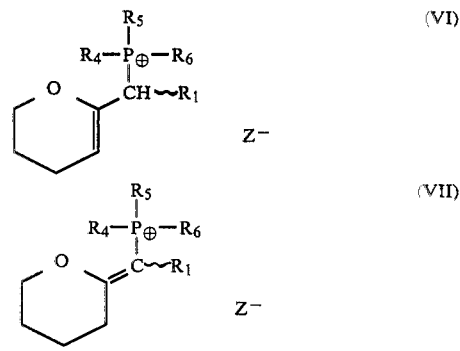

Similar pairs of isomers can result when products of formulas III or V are obtained using the methods of U.S. Pat. No. 4,075,407. These isomers can be readily separated by chromatography, if desired, but separaton is not necessary in the present invention.

A conventional preparation of the compounds of the present invention when X is a halogen radical from phosphonium salts of formula II involves heating a salt of formula II in the presence of concentrated hydrohalic acid, for example hydrochoric acid, to form an cyclic protonated phosphonium salt intermediate of formula VIII.

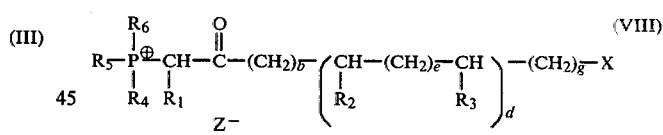

In formula VIII, $R_1$, $R_2$, $R_3$, $R_4$, $R_5$, $R_6$, b, d, e and g have the same definitions as used therefor in formulas I and II, X is a halo radical, and $Z^-$ is the anion of the radical X.

This intermediate is then dissolved in water containing potassium carbonate in excess of the amount necessary to deprotonate the phosphonium salt of formula VIII and to thereby produce a phosphorane intermediate of formula IX.

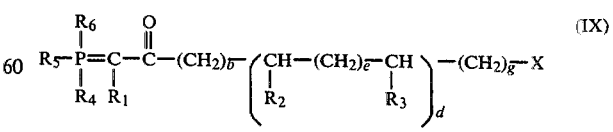

Water is then removed from the reaction mixture by extraction of the deprotonated intermediate of formula IX into an organic solvent such as benzene or methylene chloride and by subsequent drying of the organic phase over a drying agent such as sodium sulfate.

Benzaldehyde, furfural or cyclohexanecarbaldehyde—either unsubstituted or substituted with at least one nitro, halogen, hydroxy, alkyl, alkoxy or trifluoromethyl radical—is added to the reaction mixture, wherein upon refluxing under a nitrogen atmosphere, it reacts with the intermediate of formula IX to form a product of formula I and a trialkyl-, tricycloalkyl-, triaryl- or triarylalkylphosphine oxide which can readily be removed by a chromatographic separation. In addition, the starting heterocyclic phosphonium salt of formula II is produced from the intermediate of formula IX by a competing reaction and must be separated from the ketone of formula I.

The number and location of the substituents on the ring of the aldehyde reactant have no adverse effect on the reaction. The alkyl substituents contain from 1 to 6 carbon atoms and include methyl, ethyl, propyl, butyl, pentyl and hexyl, straight-chain and branched-chain radicals, and the alkoxy substituents contain from 1 to 4 carbon atoms and include methoxy, ethoxy, propoxy and butoxy, straight-chain and branched-chain radicals.

Alternatively, when X in formula I is a halogen radical and g is an integer from 1 to 5 and b is an integer from 0 to 4, the novel one-step method of this invention can be used to prepare the compounds of this invention as well as a trialkyl-, tricyclohexyl-, triaryl-, or triarylkylphosphine oxide, which can readily be removed by a chromatographic separation, for example, on a silica column.

In the method of the present invention, a heterocyclic phosphonium salt of formula X and benzaldehyde, furfural or cyclohexanecarbaldehyde—each either unsubstituted or substituted with at least one nitro, halogen, hydroxyl, alkyl, alkoxy or trifluoromethyl radical—are directly condensed in a neutral aprotic medium.

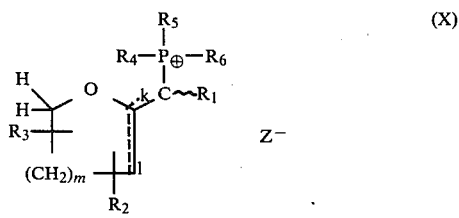

(X)

In formula X, $R_1$, $R_2$, $R_3$, $R_4$, $R_5$, $R_6$, k, l and m are as defined in formula II except that $R_2$ and $R_3$ cannot be attached to a carbon atom adjacent the oxygen atom in the ring. Further $z^-$ is the anion of the radical X.

The alkyl radical substituents on the aldehyde reactant contain 1 to 6 carbon atoms and include methyl, ethyl, propyl, butyl, pentyl and hexyl, straight-chain and branched-chain radicals. The alkoxy radical substituents on the aldehyde reactant contain 1 to 4 carbon atoms and include methoxy, ethoxy, propoxy and butoxy, straight-chain and branched-chain radicals. Apart from the limitation above noted that $R_2$ and $R_3$ cannot be attached to a carbon atom adjacent the oxygen atom in the ring, the number and location of these substituents on the ring of the aldehyde reactant have no adverse effect on the formation of the desired product by the direct condensation reaction. Preferably, a benzaldehyde or furfural or more preferably 4-nitrobenzaldehyde or 3,5-dimethoxybenzaldehyde is used.

The condensation is performed at a temperature of at least 100° C. and preferably at least 140° C., by refluxing the reactants in an inert aprotic medium. Suitable for the aprotic medium are toluene, xylene, tetrachloroethane, dioxane, dimethylformamide, sulfolane, nitromethane or benzylcyanide. In a preferred embodiment, the condensation is performed under an inert atmosphere, for example nitrogen.

The method of this invention for the formulation of compounds of this invention of formula I directly with phosphonium salts of formula X offers clear advantages over the conventional preparation involving the formation of intermediates of formulas VIII and IX. The method of this invention is a one-step preparation rather than a multi-step procedure. The present invention also involves no water or base contamination, the direct condensation thus being neutral to both reactants and suitable with aldehydes that are sensitive to basic or protic solvents. Further, the direct condensation of this invention does not involve the competing reaction regenerating heterocyclic phosphonium salt and separation of this regenerated starting material. Thus, the present invention permits maximum utilization of the phosphonium salt starting material for the formation of the intended product of formula I and requires removal of only the neutral aprotic medium and trisubstituented phosphine oxide. The aprotic medium also need not be a solvent for the phosphonium salt reactant. In addition, on an equivalent weight basis, either the salt or the aldehyde reactant can be employed in excess, and either isomer of the heterocyclic salt can be used. Furthermore, trialkyl phosphonium salts may be used to advantage because the phosphine oxide by-products therefrom are extractable by water whereas the phosphine oxides formed from triaryl phosphonium salts are generally removed by a chromatographic procedure.

Compounds of formula I wherein X is a hydroxy radical cannot be formed by the above-described novel one-step procedure. Instead such compounds are prepared by reacting the above-described benzaldehyde, furfural or cyclohexanecarbaldehyde reactant with a phosphorane or salt thereof of formulas IX and VIII, respectively, wherein X is a hydroxy radical. Compounds of formulas VIII and IX and X being a hydroxy radical are previously unreported. Compounds of formula VIII wherein X is a hydroxy radical can be prepared by reacting a lactone or formula XI with a phosphorane of formula XII.

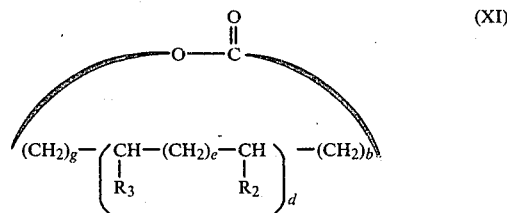

(XI)

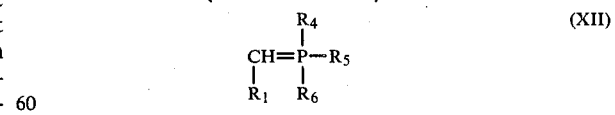

(XII)

Initially a methyl-trisubstituted phosphonium halide of formula XIII, for example, methyl-triphenylphosphonium bromide, is reacted with a strong base, for example, an alkyl lithium, preferably phenyl lithium at −78° C., or sodium amide at −33° C., under an inert atmosphere such as argon to form a phosphorane of formula XII.

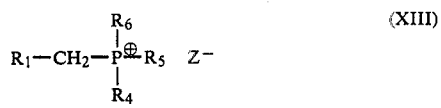

In formula XIII, $R_1$, $R_4$, $R_5$, and $R_6$ are as defined in formula II and $Z^-$ is a halide ion. The phosphorane then is reacted with a lactone of formula XI at about 10°–30° C. in an aprotic solvent or solvent mixture and under an inert atmosphere to form a phosphorane of formula IX having a hydroxy radical as X. In addition, phosphine oxide can be formed. This product mixture is then purified by extraction from an aqueous solution with an organic solvent which is thereafter removed, having the product mixture. The products can be separated conveniently chromatographically, for example, on a silica column.

Once formed, a compound of formula IX having a hydroxy radical as X can react with dilute hydrochloric acid or with concentrated hydrochloric acid to form, respectively, a heterocyclic phosphonium salt of formula II having a chloride anion as $Z^-$ or an acyclic phosphonium salt of formula VIII, having a chloride radical as X and a chloride anion as $Z^-$, both being useful as starting materials in the syntheses described above for the compounds of this invention.

The following examples describe in detail compounds illustrative of the present invention and methods which have been devised for their preparation. Throughout the examples hereinafter set forth, relative amounts of materials are given in parts by weight.

EXAMPLE 1

1.35 parts of [(5,6-dihydropyran-2-yl)methyl] triethylphosphonium chloride were suspended and 1.79 parts of 3,5-dimethoxybenzaldehyde were dissolved in 36 parts of reagent grade xylene as an inert aprotic medium. This mixture was maintained under a nitrogen atmosphere and was refluxed for 24 hours. After the reaction mixture was cooled and washed with water, the organic phase was dried over sodium sulfate, a drying agent. After separation of the drying agent, xylene was removed at 40°–50° C. and under reduced pressure, leaving a product mixture. This mixture was separated chromatographically on a silica column using increasing concentrations of ethyl acetate in cyclohexane as the elution solvent system, to yield, in the fractions containing 2 percent by volume ethyl acetate in cyclohexane, 1-(3,5-dimethoxyphenyl)-7-chloro-1-hepten-3-one which, after recrystallization from benzene, melted at about 75°–76° C.

EXAMPLE 2

2 parts of [tetrahydro-2H-pyran-2-ylidene)methyl]triphenylphosphonium chloride were suspended and 1.52 parts of 4-nitrobenzaldehyde were dissolved in 45 parts of reagent grade xylene. This mixture was maintained under a nitrogen atmosphere and was refluxed for about 24 hours, and then was cooled to room temperature, leaving a clear solution. Xylene was then removed at a temperature of about 60° C. under reduced pressure. The remaining traces of xylene were removed at about 50° C. and under a reduced pressure of about 0.5 millimeter of mercury in a drying oven, leaving a product mixture. This mixture was separated chromatographically on a silica column using as an elution solvent a mixture of increasing concentrations of benzene in Skelly B, to yield in the fractions containing 100 percent by volume of benzene 1-(4-nitrophenyl)-7-chloro-1-hepten-3-one which, following recrystallization from toluene, melted at about 70°–72° C.

EXAMPLE 3

1.13 parts of [(2-oxepanylidene)methyl] triphenylphosphonium bromide having the formula

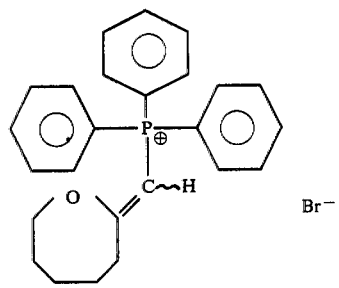

was suspended and 0.83 part of 3,5-dimethoxybenzaldehyde was dissolved in 45 parts of xylene as the aprotic medium. This mixture was maintained under a nitrogen atmosphere and was refluxed for 24 hours and was then cooled to room temperature. Xylene was removed from the resulting clear solution at a temperature of about 60° C. and under reduced pressure. The remaining traces of xylene were removed in a drying oven at a temperature of about 50° C. and under a reduced pressure of about 0.5 millimeter of mercury. The resulting product mixture was separated chromatographically in a silica gel column using a benzene elution solvent, to isolate 1-(3,5-dimethoxyphenyl)-8-bromo-1-octen-3-one which, after recrystallization from benzene, melted at about 73°–76° C.

EXAMPLE 4

39.5 parts of [(tetrahydro-2H-furan-2-ylidene)methyl] triphenylphosphonium chloride of the following formula

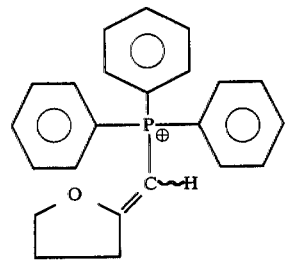

2.12 parts of benzaldehyde and 0.82 part of anhydrous sodium acetate were combined in 960 parts of tetrachloroethane. This mixture was maintained under a nitrogen atmosphere and was refluxed for 2.5 days. After the reaction mixture was cooled to room temperature, the tetrachloroethane was removed at a temperature of about 60° C. and under reduced pressure. The residue was extracted with benzene, and the organic phase was washed with water and then dried over sodium sulfate. After removal of the drying agent, the benzene was removed under a nitrogen steam, to yield a product mixture. This mixture was separated chromatographically on a silica column using an elution solvent of 5 percent by volume of isopropyl alcohol in cyclohexane, to yield 1-phenyl-6-chloro-1-hexen-3-one.

EXAMPLE 5

2 parts of [(tetrahydro-2H-pyran-2-ylidene)methyl] triphenylphosphonium chloride was suspended and 1.66 parts of 3,5-dimethoxybenzaldehyde was dissolved in 45 parts of xylene. This mixture was maintained under a nitrogen atmosphere and was refluxed for about 24 hours. After the reaction mixture was cooled to room temperature, xylene was removed from the resulting clear solution at a temperature of about 60° C. under reduced pressure. The remaining traces of xylene were removed in a drying oven at about room temperature and under a reduced pressure of about 0.5 millimeter of mercury, leaving a product mixture. This mixture was separated chromatographically on a silica column using increasing amounts of benzene in Skelly B as the elution solvent, to yield in the fraction containing 75 percent by volume of benzene in Skelly B 1-(3,5-dimethoxyphenyl)-7-chloro-1-hepten-3-one which, after recrystallization from toluene, melted at about 75°–76° C.

EXAMPLE 6

2 parts of [(tetrahydro-2H-pyran-2-ylidene)methyl] triphenylphosphonium chloride and 1.85 parts of 3-bromobenzaldehyde were combined in 45 parts of xylene. This was maintained under a nitrogen atmosphere and was refluxed for 3 hours. After the reaction mixture was cooled to room temperature, xylene was removed at a temperature of about 60° C. and under reduced pressure, leaving a product mixture. This mixture was separated chromatographically on a silica column using benzene as the elution solvent, to yield 1-(3-bromophenyl)-7-chloro-1-hepten-3-one.

EXAMPLE 7

2 parts of [(tetrahydro-2H-pyran-2-ylidene)methyl] triphenylphosphonium chloride and 1.96 parts of 2,4,5-trimethoxybenzaldehyde were combined in 45 parts of xylene. This mixture was maintained under a nitrogen atmosphere and was refluxed for 24 hours. After the resulting clear solution was cooled to room temperature, xylene was removed at a temperature of about 60° C. and under reduced pressure. The remaining traces of xylene were removed in a drying oven at about room temperature and under a reduced pressure of about 0.5 millimeter of mercury, to yield a product mixture. This mixture was separated chromatographically on a silica column using as the elution solvent increasing concentration of ethyl acetate in benzene, to yield in the fractions containing 2 percent by volume of ethyl acetate in benzene 1-(2,4,5-trimethoxyphenyl)-7-chloro-1-hepten-3-one.

EXAMPLE 8

2 parts of [(tetrahydro-2H-pyran-2-ylidene)methyl] triphenylphosphonium chloride and 1 part of furfural were combined in 45 parts of xylene. This was maintained under a nitrogen atmosphere and was refluxed for about 24 hours to give a black solution. After cooling the reaction mixture to room temperature xylene was removed from this solution at a temperature of about 40°–60° C. under reduced pressure, leaving a product mixture. This mixture was seprated chromatographically on a silica column using as the elution solvent a solution of 20 percent by volume of ethyl acetate in Skelly B, to yield 1-(2-furyl)7-chloro-1-hepten-3-one which, after a recrystallization from n-pentane, melted at about 50°–52° C.

EXAMPLE 9

2 parts of [(tetrahydro-2H-pyran-2-ylidene)methyl] triphenylphosphonium chloride and 0.82 part of 4-methylbenzaldehyde were combined in 45 parts of xylene. This suspension was maintained under a nitrogen atmosphere and was refluxed for 4.5 hours to produce a clear solution. After the solution was cooled to room temperature, the xylene was removed at a temperature of about 40° C., under reduced pressure to yield a product mixture. This mixture was separated chromatographically on a silica column using as an elution solvent increasing concentrations of ethyl acetate in toluene, to yield 1-(4-methylphenyl)-7-chloro-1-hepten-3-one in the fraction containing 1.5 percent by volume of ethyl acetate in toluene which, after recrystallization from cyclohexane, melted at about 79°–82° C.

EXAMPLE 10

2 parts of [(tetrahydro-2H-pyran-2-ylidene)methyl] triphenylphosphonium chloride was suspended and 1.4 parts of 2-chlorobenzaldehyde were dissolved in 45 parts of xylene. This mixture was maintained under a nitrogen atmosphere and was refluxed for about 4.5 hours to form a clear solution. After cooling this solution, xylene was removed at a temperature of about 35° C. under reduced pressure, to yield a product mixture. This mixture was separated chromatographically on a silica column using as the elution solvent increasing amounts of toluene in Skelly B, to yield in the fraction containing 25 percent by volume of toluene in Skelly B, 1-(2-chlorophenyl)-7-chloro-1-hepten-3-one.

EXAMPLE 11

2 parts of [(tetrahydro-2H-pyran-2-ylidene)methyl]-triphenylphosphonium chloride and 1.2 parts of cyclohexanecarboaldehyde were combined in 45 parts of xylene. This suspension was maintained under a nitrogen atmosphere and was refluxed for about 4 hours until a clear solution formed. After cooling the solution to room temperature, xylene was removed at a temperature of about 60° C. and under reduced pressure, leaving a product mixture. This mixture was separated chromatographically on a silica column using as the elution solvent 50 percent by volume of Skelly B in benzene, to yield 1-cyclohexyl-7-chloro-1-hepten-3-one.

EXAMPLE 12

2.05 parts of [(tetrahydro-2H-pyran-2-ylidene)methyl] triphenylphosphonium chloride and 0.834 part of 3,5-dimethoxybenzaldehyde were combined in 45 parts of xylene. This mixture was maintained under a nitrogen atmosphere and was refluxed for about 7.5 hours at which time the formation of 1-(3,5-dimethoxyphenyl)-7-chloro-1-hepten-3-one was complete.

EXAMPLE 13

1.72 parts of (6-chloro-2-oxohexyl)-triphenylphosphonium chloride (or [(5-chloropentanoyl)methyl]-triphenylphosphonium chloride) of the following formula

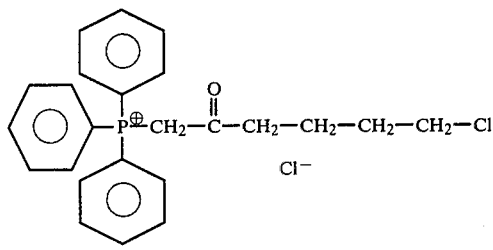

were dissolved in 30 parts of water containing an amount of potassium carbonate in excess of that necessary to deprotonate the phosphonium chloride. After extracting this solution with benzene, the organic phase was dried over sodium sulfate. After separation of the drying agent, 1.33 parts of 3,5-dimethoxybenzaldehyde were added to the dried benzene solution and this reaction mixture was refluxed for about 18 hours under a nitrogen atmosphere. After cooling to room temperature, the reaction mixture was filtered to remove crystalline [(tetrahydro-2H-pyran-2-ylidene)methyl] triphenylphosphonium chloride which is identical with the starting material of Example 2. Benzene was removed from the filtrate at a temperature of about 40° C., to yield a solid residue of reaction products. This residue was separated chromatographically using a silica column with benzene as the elution solvent, to yield 1-(3,5-dimethoxyphenyl)-7-chloro-1-hepten-3-one, which is identical to the product from Example 1.

EXAMPLE 14

71 parts of methyl triphenylphosphonium bromide was suspended in 500 parts of tetrahydrofuran with stirring and under an argon atomsphere. After this suspension was cooled to about −78° C., 17.3 parts of phenyl lithium was added dropwise over a period of about 1 hour. This solution was allowed to warm to room temperature, at which point dimethylsulfoxide was added until all salts had dissolved and the reaction mixture was clear. After stirring at room temperature, the solution was cooled to about 10° C., and about 17 parts of γ-butyrolactone was added, and the solution was stirred at room temperature for about 5 hours. This reaction mixture was combined with 1000 parts of water and stirred vigorously for 0.5 hour. After extraction with benzene, the organic phase was washed first with water and then with a saturated aqueous solution of sodium chloride in water and next dried over sodium sulfate. Benzene was removed at a temperature of about 40° C., under reduced pressure to yield (4-hydroxybutanoylmethylene)-triphenylphosphorane (or (5-hydroxy-2-oxopentyl)-triphenylphosphorane) of the following formula

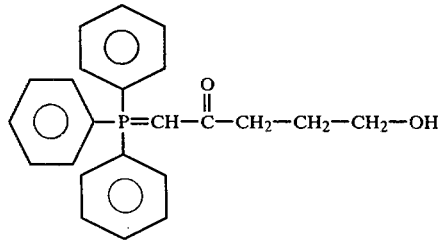

which, after recrystallization from a mixture of benzene and cyclohexane, melted at about 146°–147° C.

EXAMPLE 15

5.5 parts of the phosphorane produced in Example 14 and 3.78 parts of 3,5-dimethoxybenzaldehyde were combined in 63 parts of benzene. This solution was maintained under a nitrogen atmosphere and was stirred at room temperature for about 20 hours, at which time it was diluted with an additional 45 parts of benzene, and the solution was refluxed for about 6 hours. After cooling the reaction mixture to room temperature, the benzene was removed under a nitrogen stream, leaving a product mixture. This mixture was separated chromatographically on a silica column using as the elution solvent ethyl acetate, to yield 1-(3,5-dimethoxyphenyl)-6-hydroxy-1-hexen-3-one which, after recrystallization from a mixture of benzene and cyclohexane, melted at about 74°–77° C.

EXAMPLE 16

7.14 parts of methyltriphenylphosphonium bromide was suspended in 90 parts of tetrahydrofuran with stirring and under an argon atmosphere. After cooling the suspension to about −78° C., 1.7 parts of phenyl lithium was added dropwise over a period of about 1 hour, at which point the solution was allowed to warm to room temperature overnight. Dimethylsulfoxide was then added until all salts had dissolved and the reaction mixture was clear. After stirring the solution at room temperature and cooling it to about 10° C., 0.8 part of δ-valerolactone was added, and the solution was stirred to room temperature for about 5 hours. This reaction mixture was combined with 1000 parts of water and stirred vigorously for about 0.5 hour. After extracting this solution with benzene, the organic phase was washed first with water and then with an aqueous solution saturated with sodium chloride and then was dried over sodium sulfate. Benzene was then removed at a temperature of about 40° C. and under reduced pressure to yield (5-hydroxy-pentanoylmethylene)-triphenylphosphorane which melted at about 121°–124° C. and is represented by the following formula. This phosphorane was converted to (6-hydroxy-2-oxohexyl)-triphenylphosphonium chloride by treatment with 1 normal hydrochloric acid.

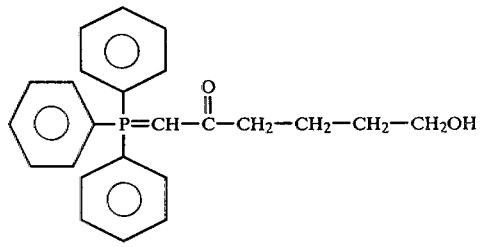

EXAMPLE 17

10 parts of the phosphonium salt produced in Example 16 was dissolved in water containing an amount of potassium carbonate in excess of that necessary to deprotonate the phosphonium chloride. After extracting this solution with methylene chloride, the organic phase was dried over sodium sulfate. After separation of the drying agent, the methylene chloride was removed at room temperature and under a stream of nitrogen, leaving (5-hydroxypentanoylmethylene)-triphenylphosphorane. 7.04 parts of this phosphorane and 3.11 parts of 3,5-dimethoxybenzaldehyde were dissolved in about 135 parts of benzene, and the solution was maintained under a nitrogen atmosphere and refluxed for 3 days. After the reaction mixture was cooled to room temperature, the benzene was removed at room temperature under a nitrogen stream, leaving a product mixture. This mixture was separated chromatographically on a silica column using as the elution solvent a mixture of 30 percent by volume of ethyl acetate in benzene, to yield 1-(3,5-dimethoxyphenyl)-7-hydroxy-1-hepten-3-one which, after recrystallization from a mixture of benzene and cyclohexane, melted at about 78°-80° C.

EXAMPLE 18

22 parts of methyl-triphenylphosphonium bromide was suspended in 180 parts of tetrahydrofuran with stirring and under an argon atmosphere. After the suspension was cooled to about −78° C., 5.4 parts of phenyl lithium was added dropwise over a period of about 1 hour. After allowing the solution to warm to room temperature overnight, dimethylsulfoxide was added until all salts had dissolved and the reaction mixture was clear. After stirring the solution at room temperature and then cooling it to about 10° C., 5.5 parts of 4-(p-fluorophenyl)-butyrolactone was added and the solution was stirred at room temperature for about 5 hours. This reaction mixture was combined with 1000 parts of water and the resulting solution was stirred vigorously for about 0.5 hour. After extracting with benzene, the organic phase was washed with water and then with an aqueous solution saturated with sodium chloride and was dried over sodium sulfate. Benzene was then removed at a temperature of about 40° C., to yield a solid mixture. This mixture was separated chromatographically on a silica column using a solution of 40 percent by volume of methylene chloride in ethyl acetate as the elution solvent, to yield [4-hydroxy-4-(4-fluorophenyl-butanoylmethylene]triphenylphosphorane which is represented by the following formula

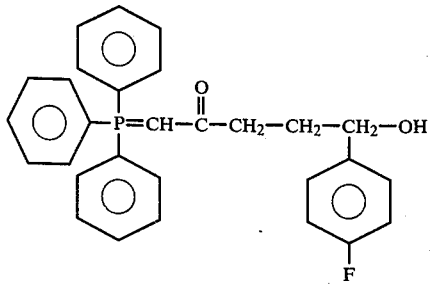

EXAMPLE 19

A solution of 18.5 parts of the final product of Example 18 in 100 parts of concentrated hydrochloric acid is refluxed for about 36 hours and then is cooled to room temperature. The solvent is removed by distillation under reduced pressure to afford 5-chloro-5-(p-fluorophenyl)-2-oxopentyltriphenylphosphonium chloride having the formula

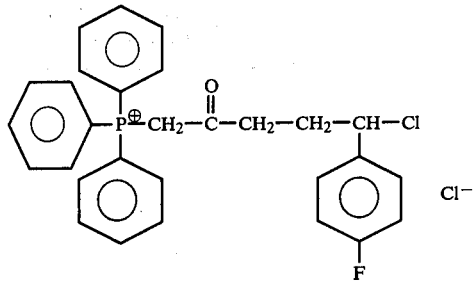

EXAMPLE 20

After refluxing a solution of 1.6 parts of the final product of Example 18 in 48 parts of methanol containing 4.0 parts of concentrated hydrochloric acid, the reaction mixture is diluted with water and the resulting solution is extracted with tetrachloroethylene. The organic phase is then dried over sodium sulfate and next the solvent is removed under a stream of nitrogen and then by heating at 50° C. for 1 hour under 0.5 millimeter of mercury, leaving a product having the formula

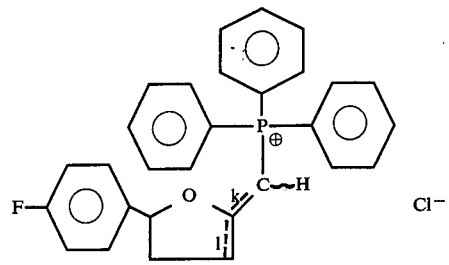

k and l have the same meaning as in formula II.

EXAMPLE 21

22 parts of methyl-triphenylphosphonium bromide were suspended in 180 parts of tetrahydrofuran with stirring and under an argon atmosphere. After cooling the suspension to about −78° C., 5.4 parts of phenyl lithium were added dropwise for a period of about 1 hour. After allowing the solution to warm to room temperature overnight, dimethylsulfoxide was added until all solids had dissolved and the reaction mixture was clear. After stirring the solution at room temperature and then cooling it to about 10° C., 4.2 parts of 1-(3H)-isobenzofuranone was added and the solution was stirred at room temperature for about 5 hours. 1-(3H)-isobenzofuranone is represented by the following formula

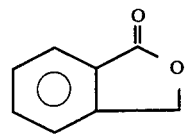

This reaction mixture was then combined with 1000 parts of water and was stirred vigorously for about 0.5 hour. After extraction with benzene, the organic phase was washed with water and with an aqueous solution saturated with sodium chloride and then dried over sodium sulfate. Benzene was removed using a rotary evaporator at a temperature of about 40° C., leaving a product mixture. This mixture was separated chromatographically on a silica column with the elution solvent being a solution of 30 percent by volume of ethyl acetate in methylene chloride, to yield a phosphorane represented by the following formula

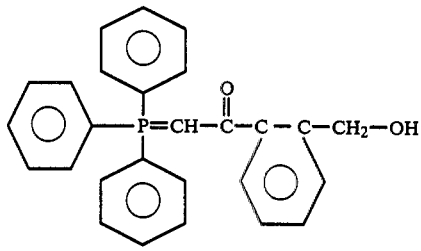

EXAMPLE 22

A solution of 18.5 parts of the final product of Example 21 in 100 parts of concentrated hydrochloric acid is refluxed to room temperature. The solvent is removed by distillation under reduced pressure to afford a product having the formula

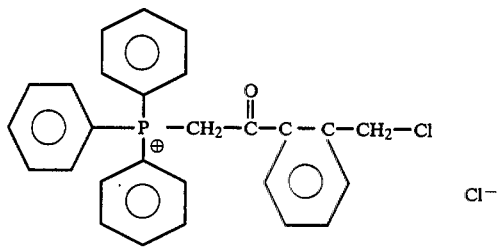

EXAMPLE 23

After refluxing a solution of 1.6 parts of the final product or Example 21 in 48 parts of methanol containing 4.0 parts of concentrated hydrochloric acid, the reaction mixture is diluted with water and the resulting solution is extracted with tetrachloroethylene. The organic phase is then dried over sodium sulfate and next the solvent is removed under a stream of nitrogen and then by heating at 50° C., for 1 hour under 0.5 millimeter of mercury leaving a product having the formula

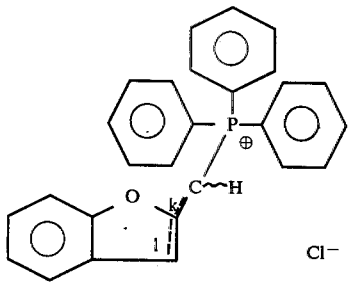

EXAMPLE 24

37 parts of ethyl -triphenylphosphonium bromide were suspended in 180 parts of tetrahydrofuran with stirring under argon atmosphere. After cooling the suspension to −78° C., 8.4 parts of phenyl lithium were added dropwise over a period of about 1 hour, at which point the solution was allowed to warm to room temperature overnight. Thereafter dimethylsulfoxide was added to the solution until all salts had dissolved and the reaction mixture was clear. After the solution was stirred to room temperature and then cooled to about 10° C., 8.1 parts of 4-phenylbutyrolactone were added and ths solution was stirred at room temperature for about 5 hours. This reaction mixture was combined with 1000 parts of water and stirred vigorously for about 0.5 hour. After extracting with benzene, the organic phase was washed with water and with an aqueous solution saturated with sodium chloride and then dried over sodium sulfate. Benzene was removed at a temperature of about 40° C., under reduced pressure, leaving a solid product mixture. This mixture was separated chromatographically on a silica column using as the elution solvent increasing concentrations of ethyl acetate in benzene to yield, in the fraction containing 40 percent by volume of ethyl acetate in benzene, (4-hydroxy-4-phenylbutanoyl-ethylidene)triphenylphosphorane having the following formula

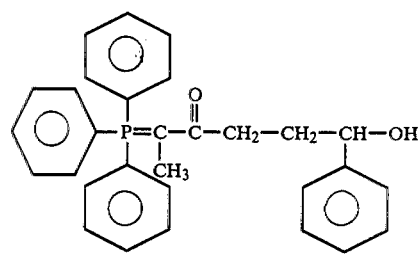

It will be apparent to those skilled in the art that while only certain embodiments are set forth herein, alternative embodiments and various modifications, both of materials and methods, are apparent from the above description and examples and are considered equivalents.

Having described the invention, what is claimed is:
1. A process for producing a compound of the formula

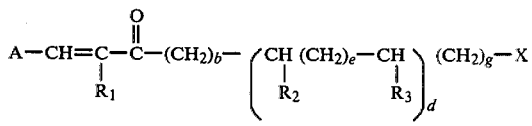

wherein A is a phenyl, furyl or cyclohexyl radical, each being either unsubstituted or substituted with at least one nitro, halogen, hydroxy, alkyl, alkoxy or trifluoromethyl radical with each alkyl radical being a straight-chain or branched-chain group containing from 1 to 6 carbon atoms and with each alkoxy radical being a straight-chain or branched-chain group containing from 1 to 4 carbon atoms; $R_1$ is hydrogen or a methyl radical; b is an integer from 0 to 4; g is an integer from 1 to 5; d and e are each 0 or 1; the sum of b, e, g and 2d is an integer from 3 to 5; when e is 0 or 1, $R_2$ and $R_3$ are each a hydrogen, methyl, ethyl or phenyl radical, the phenyl radical being unsubstituted or substituted with at least one halo or alkyl radical containing from 1 to 3 carbon atoms or, when e is 0, $R_2$ and $R_3$ are interconnected to form, together with the intervening ethylene radical, a phenyl ring that is unsubstituted or substituted with at least one halogen or alkyl radical containing from 1 to 3 carbon atoms; and X is halogen comprising directly condensing in a neutral aprotic medium a benzaldehyde, furfural or cyclohexane-carbaldehyde with a heterocyclic phosphonium salt having the formula

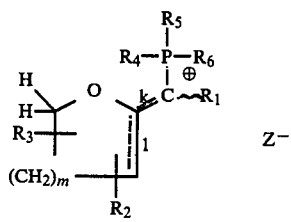

wherein m is an integer from 1 to 3; one of k and l is a double bond and the other is a single bond; $Z^-$ is a halide anion; $R_2$ and $R_3$ are attached either to adjacent carbon atoms on the ring or to carbon atoms on the ring separated by only one carbon atom, $R_4$, $R_5$ and $R_6$ are the same or different and are each an alkyl radical containing 1 to 6 carbon atoms, a cycloalkyl radical containing 5 or 5 carbon atoms or a radical having the formula

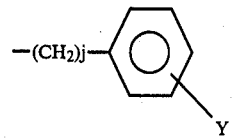

wherein j is an integer from 0 to 4 and Y is hydrogen, halogen or an alkyl radical containing 1 to 6 carbon atoms, or an alkoxy radical containing 1 to 4 carbon atoms, and said aldehyde reactant being unsubstituted or substituted with at least one nitro halogen, hydroxy, straight-chain or branched-chain alkyl, containing 1 to 6 carbon atoms, straight-chain or branched-chain alkoxy containing 1 to 4 carbon atoms, or trifluoromethyl radical.

2. The process of claim 1 wherein said condensation is performed at a temperature of at least 100° C.

3. The process of claim 1 wherein said condensation is performed at a temperature of at least 140° C.

4. The process of claim 1 wherein said condensation is performed under an inert atmosphere.

5. The process of claim 1 wherein said neutral aprotic medium comprises at least one of toluene, xylene, tetrachlorocthylene, dioxane, dimethylformamide, sulfolane, nitromethane or benzylcyamide.

6. The process of claim 1 wherein $Z^-$ is a bromide or chloride ion.

7. The process of claim 1 wherein $R_4$, $R_5$ and $R_6$ are ethyl radicals.

8. The process of claim 1 wherein $R_4$, $R_5$ and $R_6$ are phenyl radicals.

* * * * *